(12) United States Patent
Lin et al.

(10) Patent No.: US 7,247,299 B2
(45) Date of Patent: Jul. 24, 2007

(54) **ANTIMICROBIAL COMPOUNDS FROM *BACILLUS SUBTILIS* FOR USE AGAINST ANIMAL AND HUMAN PATHOGENS**

(75) Inventors: Angeline Seah Huay Lin, Singapore (SG); Alex Yeow-Lim Teo, Singapore (SG); Tan Hai Meng, Singapore (SG)

(73) Assignee: Kemin Industries, Inc., Des Moines, IA (US)

( * ) Notice: Subject to any disclaimer, the term of this patent is extended or adjusted under 35 U.S.C. 154(b) by 456 days.

(21) Appl. No.: 10/306,365

(22) Filed: Nov. 27, 2002

(65) Prior Publication Data

US 2004/0101525 A1    May 27, 2004

(51) Int. Cl.
*A01N 63/00* (2006.01)

(52) U.S. Cl. .................. 424/93.46; 435/252.5

(58) Field of Classification Search ............ None
See application file for complete search history.

(56) References Cited

U.S. PATENT DOCUMENTS

| | | | | |
|---|---|---|---|---|
| 4,968,493 | A | * 11/1990 | Carter et al. ............ | 424/122 |
| 5,352,586 | A | * 10/1994 | Dobrogosz et al. ........ | 435/34 |
| 5,364,788 | A | 11/1994 | Kubo | |
| 5,407,917 | A | * 4/1995 | Hart ........................ | 514/25 |
| 2002/0048576 | A1* | 4/2002 | Anderson et al. ......... | 424/94.63 |

FOREIGN PATENT DOCUMENTS

| EP | 0 128 505 A | 12/1984 |
|---|---|---|
| WO | WO 99/28441 A | 6/1999 |

OTHER PUBLICATIONS

Alander, M., R. Satokari, R. Korpela, M. Saxelin, T. Vilpponen-Salmela, T. Mattila-Sandholm, and A. von Wright. 1999. Persistence of colonization of human colonic mucosa by a probiotic strain, *Lactobacillus rhamnosus* GG, after oral consumption. 65:351-351.
Andersson, R.E. 1986. Inhibition of *Staphlococcus aureus* and spheroplasts of gram-negative bacteria by antagonistic compound produced by a stain of *Lactobacillus plantarum*. Int. J. Food Microbiol. 3:149-160.
Asensio, C., J.C. Perez-Diaz, M.C. Martinez, and F. Baquero. 1976. A new family of low molecular weight antibiotics from enterobacteria. Biochem. Biophys. Res. Commun. 69:7-14.
Barnes, E.M., G.C. Meads, D.A. Barnum, and E.G. Harry. 1972. The intestinal flora of the chicken in the period 2 to 6 weeks of age, with particular reference to the anaerobic bacteria. Br. Poult. Sci. 13:311-326.
Barrow, P.A., B.E. Brooker, R. Fuller, and M.J. Newport. 1980. The attachment of bacteria to the gastric epithelium of the pig and its importance in the microecology of the intestine. J. Appl. Bacteriol. 48:147-154.
Charteris, W. P., P.M. Kelly, L. Morelli, and J.K. Collins. 1997. Selective detection, enumeration and identification of potentially probiotic *Lactobacillus* and *Bifidobacterium* species in mixed bacterial population. Int. J. Food Microbiol. 35:1-27.
Council of the European Communities. 1998 Regulation EEC No. 2821/98. Off. J. Eur. Commun., L351/4.
Cowen, B.S., L.D. Schwatz, R.A., Wilson, and S.I. Ambrus. 1987. Experimentally induced necrotic enteritis in chickens. Avian Dis. 31:904-906.
Craven, S.E., N.J. Stem, N.A. Cox, J.S. Bailey, and M. Berrang. 1999. Cecal carriage of *Clostridium perfringens* in broiler chicken given Musocal Starter Culture . Avian Dis. 43:484-490.
Devriese, L., A. G. Daube, J. Hommez, and F. Haesebrouck. 1993. In vitro susceptibility of *Clostridium perfringes* isolated from farm animals to growth-enhancing antibiotics. J. Appl. Bacteriol. 75:55-57.
Donohue, D.C., and S. Salminen. 1996. Safety of probiotic bacterial. Asia Pac. J. Clin. 5:25-28.
Drake, M., C.L. Small, K.D. Spence, and B.G. Swanson. 1996. Rapid detection and identification of *Lactobacillus* spp. in dairy products by using polymerase chain reaction. J. Food Prot. 59:1031-1036.
Ersfeld-Dressen, H., H.-G. Sahl, and H. Brandis. 1984. Plasmid involvement in production of and immunity to the staphylococcin-like peptide Pep 5. J. Microbiol. 130:3029-3035.
Fleming, H.P., J.L. Etchells, and R. N., Costilow. 1975. Microbial inhibition by isolate of Pediococcus from cucumber brines. Appl. Microbiol. 30:1040.
Fuller, R. 1073. Ecological studies on the *Lactobacillus flora* associated with the crop epithelium of the fowl, J. Appl. Bacteriol. 36:131-139.
Fuller, R. 1989. Probiotics in man and animals. J. Appl. Bacteriol. 66:365-378. Gilliand, S.E., and M.L. Speck 1974. Inhibition of psychotrophic bacteria by lactic acid bacteria in nonfermented refrigerated foods. Paper presented at the 34th Annual IFT Meeting, New Orleans.
Graham, D.C., and L.L. McKay. 1985. Plasmid, DNA in strains of *Pediococcus cerevisiae* and *Pediococcus pentosaceus*. Appl. Environ. Microbiol. 50:532. Gross, E., and J.L. Morell. 1971. The structure of nisin. J. Am. Chem. Soc. 93:4634-4635.
Hale, O.M., and G.I. Newton. 1979. Effects of a nonviable *Lactobacillus* species fermentation product on performance of pigs. J. Anim. Sci. 48:770-775.
Harris, L.J., M.A. Daeschel, M.E. Stiles, and T.R. Klaenhammer. 1989. Antimicrobial activity of lactic acid bacterial against Listeria monocytogenes. J. Food Prot. 53:384-387.
Hoa, N. T., L. Baccigalupi, A. Huxham, A., Smertenko, P. H. Van, S. Ammendola, E. Ricca, and S. M. Cutting. 2000. Characterization of *Bacillus* species used for oral bacteriotheray and bacterioprophylaxis of gastrointestinal disorders. Appl. Environ. Microbiol. 66:5241-5247.

(Continued)

*Primary Examiner*—Irene Marx
(74) *Attorney, Agent, or Firm*—Kent A. Herink; Emily E. Harris

(57) ABSTRACT

Antimicrobial compounds from *Bacillus subtilis* for use against animal and human pathogens. A novel strain of *Bacillus subtilis* was isolated from the gastrointestinal tract of poultry and was found to produce a factor or factors that have excellent inhibitory effects on *Clostridium perfringens, Clostridium difficile, Campylobacter jejuni, Campylobacter coli*, and *Streptococcus pneumoniae*. The factor(s) retain full viability and antimicrobial activity after heat treatment. The invention provides a method of treatment of pathogenic microorganisms including *C. perfringens*.

6 Claims, 1 Drawing Sheet

OTHER PUBLICATIONS

Hofacre C.L., R. Froyman, B. Gautrias, B. George, M.A. Goodwin, and J. Brown. 1998. Use of Aviguard and other intestinal bioproducts in experimental Clostridium perfringens-associated necrotizing enteritis in broiler chickens. Avian Dis. 42:579-584.

Horner, T., H. Zahner, R. Kellner, and G. Jung. 1989. Fermentation and isola-tion of epidermin, a lanthionine containing polypeptide antibiotic from *Staphylococcus aureus*. Appl. Microbiol. and Biotechnol. 30:219-225.

Hosoi, T., A. Ametani, K. Kiuchi, and S. Kaminogawa. 2000. Improved growth and viability of lactobacilli in the presence of *Bacillus subtilis* (natto), catalase, or subtilin. Can. J. Microbiol. 46:892-897.

Huis In't Veld, J.H.J., and C. Shortt. 1996. Selection criteria for probiotic microorganisms. R. Soc. Med. Int. Congr. Symp. Ser. 219:27-36.

Jansen, E.F., and D.J. Hirschmann. 1944. Subtilin, an antibacterial substance of *Bacillus subtilis*: culturing condition and properties. Arch. Biochem. 4:297-309.

Jin, L.Z., Y.W. Ho, N. Abdullah, H. Kudo, and S. Jalaludin. 1997. Studies on the intestinal microflora of chicken under tropical conditions. AJAS, 10 (5) 495-504.

Juffs, H.S., and F. J. Babel. 1975. Inhibition of psychrotrophic bacteria by lactic cultures in milk stored at low temperature. J. Dairy Sci. 58:1612-1619.

Kaldhusdal, M. I. 2000. Necrotic enteritis as affected by dietary ingredients. World Poultry-Elsevier. 16 (6) 42-43.

Kondo, F. 1988. In vitro lecithinase activity and sensitivity of 22 antimicrobial agents of *Clostridium perfringens* isolated from necrotic enteritis of broiler chickens. Res. Vet. Sci. 45:337-340.

Konisky, J. 1982. Colicins and other bacteriocins with established modes of action. Ann. Rev. Microbiol. 36:125.

Kordel, M., F. Schüller and H.-G. Sahl. 1989. Interaction of the pore forming-peptide antibiotics Pep 5, nisin and subtilin with non-energized liposomes. J. Fed. Eur. Biochem. Soc. Lett. 244:99-102.

Kordel, M., and H-G. Sahl. 1986. Susceptibility of bacterial, eukaryotic and artificial membranes to the disruptive action of the cationic peptides Pep 5 and nisin. FEMS Microb. Lett. 34:139-144.

Lee, Y.K., K. Nomoto, S. Salminen, and S.L. Gorbach. 1999. Handbook of Probiotics. John Wiley & Sons: USA.

Mead, G.C. 1997. Bacteria in the intestinal tract of birds, p. 216-240, In R.I. Mackie, B.A. White, and R.E. Isaacsson (ed.), Gastrointestinal microbiology. 2. Gastrointestinal microbes and host interactions. Chapman & Hall, New York, N.Y.

Mead, G.C., and B.W. Adams. 1975. Some observations on the cecal microflora of the chick during the first two weeks of life. Br. Poult. Sci. 16:169-176.

Mitchell, D.I. and R. Kenworth. 1976. Investigations on a metabolite from *Lactobacillus bulgaricus* which neutralizes the effect of enterotoxin from *Escherichia coli* pathogenic for pigs. J. Appl. Bacteriol. 41:163-174.

Morishita, T.Y., P.P. Aye, B.S. Harr, C.W. Cobb, and J.R. Clifford. 1997. Evaluation of an avian-specific probiotic to reduce the colonization and shedding of *Campylobacter jejuni* in broilers. Avian Dis. 41:850-855.

Motlagh, A.M., M.C. Johnson, and B. Ray. 1991. Viability loss of foodborne pathogens by starter culture metabolites. J. Food Prot. 54:873-878.

Muriana, Peter M. 1993. Antimicrobial peptides and their relation to food quality. p. 303-321, Ch. 24 in "Food Flavor and Safety." American Chemical Society, Washington, D.C.

Naclerio, G., E. Ricca, M. Sacco, and M.D. Felice. 1993. Antimicrobial activity of a newly identified bacteriocin of *Bacillus cereus*. Appl. Environ. Microbiol. 59:4313-4316.

Paik, H.-D., N.-K. Lee, H.-K. Lee, Y.-I. Hwang, and J.-C. Pan. 2000. Identification and partial charcterization of cerein BS229, bacteriocin produced by *Bacillus cereus* BS229. J. Microbiol. Biotechnol. 10:195-200.

Paik, H.-D., S.-S. Bae, S.-H. Park, and J.-G. Pan. 1997. Identification and partial characterization of tochicin, a bacteriocin produced by *Bacillus thuringiensis* subsp. tochigiensis. J. Ind. Microbiol. Biotechnol. 19:294-298.

Pascual, M., M. Hugas, J.I. Badiola, J.M. Monfort, and M. Garriga. 1999. *Lactobacillus salivarius* CTC2197 prevents *Salmonella enteritidis* colonization in chickens. 65:4981-4986.

Pattnaik, P., J.K. Kaushik, S. Grover, and V.K. Batish. 2001. Purification and characterization of a bacteriocin-like compound (Lichenin) produced by anaerobically by *Bacillus licheniformis* isolated from water buffalo. J. Appl. Microbiol. 91:636-645.

Ratcliff, J. 2000. British supermarkets: Forging changes in poultry nutrition. Proc. Aust. Poult. Sci. Sym. 25-31.

Reid, G. 1999. The scientific basis for probiotic stains of *Lactobacillus*. Appl. Environ. Microbiol. 65:3763-3766.

Roller, S. 1991. The biotechnological development of new food preservatives. Biotechnol. Gen. Engin. Rev. 9:183-206.

Sahl, H.-G. 1985. Bactericidal cationic peptides involved in bacterial antagonism and host defence. Microbiol. Sci. 2(7):212-217.

Salanitro, J.P., I.G. Blake, and P.A. Muirhead. 1974. Studies on the cecal microflora of commercial broiler chickens. Appl. Microbiol. 28:439-447.

Salminen, S., E. Isolauri, and E. Salminen. 1996. Clinical uses of probiotics for stabilizing the gut mucosal barrier: successful strains and future challenges. Antonie van Leeuwenhoek. 70:347-358.

Scan. 2000. Opinion of the scientific committe on animal nutrition (SCAN) on the safety use of *Bacillus* species in animal nutrition.

Scheinbach, S. 1998. Probiotics: functionality and commercial status. Biotechnol. Adv. 16:581-608.

Schwab, C.C., J.J. III Moore, P.M. Hoyt, and J.L. Prentice. 1980. Performance and fecal flora of calves fed anonviable *Lactobacillus bulgaricus* fermentation product. J. Dairy Sci. 63:1412-1423.

Shapiro, S.K., and W.B. Saries. 1949. Microorganisms in the intestinal tract of normal chickens. J. Bacteriol. 58:531-544.

Silva, M., N. W. Jacobus, C. Deneke and S.L. Gorbach. 1987. Antimicrobial substance from a human *Lactobacillus* strain. Antimicrob. Agents Chemother. 31:1231-1233.

Sissons, J.W. 1989. Potential of probiotic organisms to prevent diarrhoea and promote digestion n farm animals—a review. J. Sci. Food Agric. 49:1-13.

Spelhaug, S.R., and S.K. Harlander. 1989. Inhibition of foodborne bacterial pathogens by bacteriocins from *Lactococcus lactis* and *Pediococcus pentosaceous*, J. Food Prot. 52:856-862.

Tagg, J.R., and A.R. McGiven. 1971. Assay system for bacteriocins. Appl. Environ. Microbiol. 21:943.

Thomke, A., and K. Elwinger. 1998. Growth promotants in feeding pigs and poultry. III. Alternatives to antibiotic growth promotants. Ann. Zootech. (Paris) 47:245-271.

Tortuero, F. 1973. Influence of the implantation of *Lactobacillus acidophilus* in chicks on the growth, feed conversion, malabsorption of fats syndrome and intestinal flora. Poult. Sci. 52:197-203.

Tournot, J. 1989. Applications of probiotics to animal husbandry. Rev. Sci. Tech. Off. Int. Epiz. 8:551-566.

Tsi, S.S., and M.C. Tung. 1981. An outbreak of necrotic enteritis in broiler chickens. J. Chinese Soc. Vet. Sci. 7:13-17.

Tshirdewahn, B., S. Notermans, K. Wernars, and F. Untermann. 1991 The presence of enterotoxigenic *Clostridium perfringens* strains in feces of various animals. Int. J. Food Microbiol. 14:175-178.

Von Tersch, M.A., and B.C. Carlton. 1983. Bacteriocin from *Bacillus megaterium* ATCC 19213: comparative studies with megacin A216. J. Bacteriol. 155:866-871.

Watkins, B.A., B.F. Miller, and D.H. Neil. 1982. In vivo effects of *Lactobacillus acidophilus* against pathogenic *Escherichia coli* in gnotobiotic chicks. Poult. Sci. 61:1298-1308.

Watkins, K.L., T.R. Shryock. R.N. Dearth, and Y.M. Saif. 1997. In-vitro antimicrobial susceptibility of *Clostridium perfringes* from commercial turkey and broiler chicken origin. Vet. Microbiol. 54:195-200.

Wesney, E., and G.W. Tannock. 1979. Association of rat, pig, and fowl biotypes of lactobacilli with the stomach of gnotobiotic mice. Microb. Ecol. 5:35-42.

West, C.A., and P.J. Warner. 1988. Plantacin, B, a bacteriocin produced by *Lactobacillus plantarum* NCDO 1193. FEMS Microbiol. Lett. 49:163.

Paik, S.H., et al., "Identification and Characterization of the structural and transporter genes for the chemical and biological properties of, sublacin 168, a novel lantibiotic produced by *Bacillus subtilis* 168", Journal of Biological Chemistry, vol. 273, No. 36, Sep. 4, 1998, p. 23134-23142.

Anderson, A.A., "Effect of *Subtilin* on spores of *Clostridium botulinum*", Journal of Bacteriology, vol. 64, No. 2, Aug. 1992, p. 145-149

Campbell, L.L., "Isolation and properties of a subtilin resistant strain of *Clostridium botulinum*" Applied Microbiology, vol. 7, Sep. 1959, p. 285-288.

Pinchuk, V., "In Vitro anti-helicobacter pylori activity of the probiotic strain *Bacillus subtilis* 3 is due to secretion of antibiotics", Antimicrobial Agents and Chemotherapy, vol. 45, No. 11, Nov. 2001, p. 3156-3161.

Miyamoto T., et al, "Effect of an antibacterial factor derived from *Bacillus-subtilis* fhc 402 on the growth of bacteria and mouse myeloma mpc-11 cells" Database Biosis (online), Philadelphia, PA, 1987.

Gusils C, et al, "*Lactobacilli* isolated from chicken intestines: potential use as probiotics" Journal of Food Protection, Des Moines IA, vol. 62, No. 3, Mar. 1999, p. 252-256.

Jack R.W., et al., *Bacteriocins* of gram-positive bacteria, Microbiological Reviews, American Society for Microbiology, Washingtoon D.C., vol. 59, No. 2, Jun. 1, 1995, p. 171-200.

Teo Alex Yeow-Lim et al, "Inhibition of clostridium perfringes by a novel strain of *Bacillus subtilis* isolated from the gastrointestinal tracts of healthy chickents", Applied and Environmental Microbiology, vol. 71, No. 8, Aug. 2005, p. 0099-2240.

* cited by examiner

[1]*Bacillus* subtilis PB6, [2]*B. subtilis* (Dupont data base strain 1), [3]*B. subtilis* PB3, [4]*B. subtilis* (Dupont data base strain 2), [5]*B. subtilis* (Dupont data base strain 3).

ANTIMICROBIAL COMPOUNDS FROM *BACILLUS SUBTILIS* FOR USE AGAINST ANIMAL AND HUMAN PATHOGENS

BACKGROUND OF THE INVENTION

This invention relates generally to antimicrobial compounds and, more specifically, to antimicrobial compounds from *Bacillus subtilis* PB6 for use against animal and human pathogens.

Necrotic enteritis, an enterotoxemic disease caused by *Clostridium perfringens* leads to the development of necrotic lesions in the gut wall resulting in mortality of poultry (Paulus and Ruckebusch, 1996; Tsai and Tung, 1981). It is also a multifactorial disease with complex and partly unknown epidemiology and pathogenesis (Kaldhusdal, 2000). The bacterium, *C. perfringens* is commonly found in the gastrointestinal tract of poultry (Tshirdewahn et al. 1991), the occurrence of necrotic enteritis, is however sporadic (Cowen et al., 1987). Nevertheless, feed contaminated with *C. perfringens* has been implicated in outbreaks of necrotic enteritis in chickens (Kaldhusdal, 2000). Studies have also shown that healthy chickens have a relatively low number of *C. perfringens* in their gastrointestinal tracts, while an increase in the concentration of the bacteria can result in a necrotic enteritis condition (Craven et al., 1999).

The use of bacitracin, linocomycin and other growth promoting antibiotics are commonly used to treat poultry suffering from necrotic enteritis (Craven et al., 1999). However, due to the isolation of antibiotic-resistant strains of *C. perfringens* from chickens and turkeys (Devriese et al., 1993; Kondo, 1988; Watkins et al., 1997), poultry health authorities and producers are increasingly interested in the development and application of probiotic products to replace antibiotics. Probiotics have been defined as a live microbial feed supplement that beneficially affects the host by improving its intestinal microbial balance. Some researchers believe that this normalization of the intestinal microbiota will confer the following benefits: (a) protection against pathogens by competitive exclusion (also termed colonization resistance); (b) provision of certain nutrients and enzymatic/detoxification reactions; (c) involvement in tissue morphogenesis and peristaltic activity; and (d) interaction with the immune and endocrine systems of the host. Furthermore, in the light of rising necrotic enteritis in poultry and the progressive ban of various feed antibiotics by many countries (Council of the European Communities, 1998), there is a shift towards alternative growth promoters (AGP) to enhance animal performance. Beneficial microorganisms, such as yeast or lactic acid bacteria have been used in animal production for the last two decades. Bacteria with probiotic attributes have the primary function of maintaining healthy gut microflora by replacing or displacing the pathogenic bacteria in the intestinal tract. It has been known that probiotics could maintain "normal" intestinal microflora through competitive exclusion (Toumot, 1989) and antagonistic action against pathogenic bacteria in the animal intestine (Fuller, 1989). Generally, probiotic microorganisms could proliferate in large numbers within the gut, thus inhibiting the multiplication of pathogenic bacteria. Probiotic microorganisms that have potential uses in humans or animals include *Bacillus* spp., *Lactobacillus* spp., *Enterococcus* spp. and *Streptococcus* spp. (Lee et al., 1999). Various microorganisms have been reported to be able to colonize different parts of the gastrointestinal tract (Jin et al., 1997). Generally, the duodenum portion of the gastrointestinal tract has the lowest population of bacterial microflora compared to the caeca, which has the highest concentration of microorganisms (Mead and Adams, 1975; Salanitro et al., 1974). Microorganisms, such as *Lactobacillus* spp., *Streptococcus* spp. and *Escherichia coli* have been isolated from the duodenum, jejunum and ileum portions of the small intestine (Shapiro and Sarles, 1949). The general microbial population of the caeca comprises obligate anaerobes such as *Streptococcus* spp., *Staphylococcus* spp., *Lactobacillus* spp., *Fusobacterium* spp. and *Bacteroides* (Barnes et al., 1972; Mead, 1997).

Beneficial bacteria from various segments of the chicken's intestinal tract were isolated and screened as potential probiotics against *C. perfringens*. Previous studies demonstrated that the ability of probiotic microorganisms to adhere and colonize the epithelial cells of the gastrointestinal tract is largely dependent on the specific site of isolates from a specific animal source (Barrow et al., 1980; Reid, 1999; Fuller, 1973; Wesney and Tannock, 1979). There are many beneficial effects associated with the use of microbial probiotics in animal feeds. These beneficial effects include the competitive exclusion of pathogenic *E. coli* (Watkins et al., 1982), *Campylobacter jejuni* (Morishita et al., 1997) and *Salmonella enteritidis* (Pascual et al., 1999), enhancing growth and viability of beneficial gut microflora (Hosoi et al., 2000), and improved digestion and absorption of nutrients (Ratcliff, 2000; Scheinbach, 1998; Sissons, 1989; Thomke and Elwinger, 1998) in chicken.

Other criteria used for isolating and defining probiotic bacteria include bile and acid stability (Hoa et al., 2000; Huis In't Veld and Shortt, 1996), production of antimicrobial substances (Salminen et al., 1996) and meeting safety or generally recognized as safe (GRAS) status (Donohue and Salminen, 1996; SCAN, 2000). A large number of lactic acid bacteria, singly or in combination, were shown to display varying degrees of antimicrobial activity toward pathogenic microorganisms (Harris et al., 1989; Motlagh et al., 1991). In addition, viable cultures or fermented extracts of lactic acid bacteria are useful in the treatment of displaced endogenous intestinal microflora, which are characteristic of many intestinal disorders (Charteris et al., 1997; Drake et al., 1996). Such bacteria are able to survive acidic and bile conditions to colonize the intestinal tract or at least temporarily, by adhering to the epithelium. They have been reported to improve the growth rate and feed utilization in pigs, chicken and calves (Hale and Newton, 1979; Tortuero, 1973; Schwab et al., 1980). In addition, a significant decrease in the occurrence of diarrhea has been observed in pigs and calves fed with these beneficial bacteria (Lee et al., 1999). Lactic acid bacterial cultures are also believed to neutralize the effect of enterotoxins from *E. coli* in pigs (Mitchell and Kenworthy, 1976). Other beneficial effects of the lactic acid bacteria include the displacement of harmful bacteria including *C. perfringens,* reduction of bacterial urease activity, synthesis of vitamins, stimulatory effects on the immune system and contribution to digestion (Hofacre et al., 1998). Previous studies have shown that *Lactobacillus rhamnosus* (Alander et al., 1999; Asensio et al., 1976; Silva et al., 1987), *L. plantarum* (Andersson, 1986; West and Warner, 1988), *Lactococcus lactis* ssp. *lactis* (Motlagh et al., 1991; Spelhaug and Harlander, 1989), and *Pediococcus pentosaceus* (Fleming et al., 1975; Graham and McKay, 1985) were bactericidal towards *Clostridium* spp.

Microbial peptides with pronounced antimicrobial activity are commonly isolated from animals, plants, microbes (Sahl, 1985) and in non-sterile food (Muriana, 1993). They are small and cationic with molecular masses between 3000 and 6000 Daltons (Roller, 1991). Post-translational modification of precursor peptides has been shown to introduce intramolecular thioether bridges to cationic peptides such as Pep 5, nisin, and subtilin (Gross and Morell, 1971; Kordel and Stahl 1986; Kordel et al., 1989). Although these peptides offer an important potential safety advantage over chemically synthesized preservatives when incorporated into food, many peptides are not suitable owing to the pathogenic nature of the producer-strains. Peptides such as colicins (Konisky, 1982), epidermin and Pep 5 (Ersfeld-Dressen et al., 1984; Homer et al., 1989) may be useful in topical application in creams and salves, but are unlikely to be approved for use in foods because of the nature of the producer-strains (Roller, 1991).

The present invention relates to cells or fermented extracts of Bacillus subtilis PB6 exhibiting antimicrobial activity against C. perfringens. Studies in our laboratory have demonstrated that the fermented extracts of Bacillus subtilis PB6 contain antimicrobial factor(s) of a proteinaceous nature that is stable under high heat, acidic condition, elevated concentrations of bile salts, and extractable in solvents. The production of bacteriocins by Bacillus spp. has been reported and the best characterized bacteriocins are subtilin of B. subtilis (Jansen and Hirschmann, 1944), megacin of B megaterium (Von Tersch and Carlton, 1983), lichenin of B. licheniformis (Pattnaik et al., 2001), tochicin of B. thuringiensis (Paik et al., 1997), and some bacteriocins of B. cereus (Naclerio et al., 1993; Paik et al., 2000). Despite the extensive screening of these bacteriocins against a wide spectrum of pathogenic microorganisms, no study has been conducted to determine the effect of cells or metabolites of Bacillus spp. on C. perfringens. Our studies have also confirmed that the fermented extracts of Bacillus subtilis PB6 were also inhibitory toward C. difficile, Campylobacter jejuni, Campylobacter coli and Streptococcus pneunoniae.

SUMMARY OF THE INVENTION

The present invention consists of a novel bacterium strain isolated from the gastrointestinal tract of poultry and its use to inhibit Clostridium spp. Specifically, Bacillus subtilis PB6 was found to possess anticlostridial factor(s) that exhibit excellent inhibitory effects on Clostridium perfringens, limiting the production of clostridial enterotoxins that cause necrotic enteritis in poultry. The invention provides a method of treatment that includes but is not limited to the destruction of C. perfringens in contaminated animal feeds fed to poultry. The invention also relates to providing a heat-resistant strain of Bacillus subtilis PB6 as well as heat stable anticlostridial factor(s) that can withstand high temperatures during the pelleting process of animal feeds. Cells of Bacillus subtilis PB6 and their anticlostridial factor(s) after heat treatment fully retain viability and antimicrobial activity. In addition, the invention provides a strain of Bacillus subtilis PB6 as well as the anticlostridial factor(s) that are stable to different pHs of gastrointestinal tract of poultry. The invention ensures passage of Bacillus subtilis PB6 and its anticlostridial factor(s) into the lower intestinal tract of infected poultry whereby C. perfringens may be displaced and/or detached and inhibited, respectively.

This invention also relates to extending the application of Bacillus subtilis PB6 and its anticlostridial factor(s) in the destruction of human pathogens including, but not limited to, the destruction of Clostridium difficile, Campylobacter jejuni, Campylobacter coli, and Streptococcus pneumoniae.

BRIEF DESCRIPTION OF THE DRAWINGS

FIG. 1 is a photograph of a petri dish showing the antagonistic assay, wherein the vertical streak was the indicator organism, Clostridium perfringens ATCC 13124 and the horizontal streaks were Bacillus subtilis PB6 and Bacillus subtilis ATCC 6633, the former isolated from the intestinal tract of healthy chicken.

FIG. 2 is a photograph of a RiboPrint™ showing digested nucleic acid profiles of Bacillus subtilis PB6. This ribotyping technique uses restriction enzymes, such as EcoR I, Pst I and Pvu II to digest DNA extracted from bacteria producing DNA fragments. A specific probe using the operon of rRNA gene is then used to detect these DNA fragments therefore confirming the strain to be the original Bacillus subtilis PB6.

DETAILED DESCRIPTION OF A PREFERRED EMBODIMENT

Materials and Methods

Identification of Putative Bacillus spp. Isolated From the Intestinal Tract of Chicken Intestinal tracts from healthy chicken were obtained from a local market that was certified by Agri-food & Veterinary Authority of Singapore (AVA). The freshly obtained intestinal tracts were dissected into 4 sections, namely the duodenum, jejunum, ileum and caeca. Contents from each segment were collected into test tubes containing sterile Tryptic Soy Broth (Becton, Dickinson & Co, MD) containing 0.6% yeast extract (Oxoid Ltd, UK) (TSBYE) (1 L TBSYE comprises 30 g Tryptic soy broth powder and 6 g yeast extract, autoclaved at 121° C. for 20 min.) and heated at 80° C. for 20 min. After heat treatment, portions from each test tube were streaked onto agar containing TSBYE (called TSAYE) (1 L TSAYE comprises 30 g Tryptic soy broth powder, 6 g yeast extract, and 10 g agar, autoclaved at 121° C. for 20 min) and incubated at 37° C. for 18-22 h. Random colonies from four quadrants were selected and inoculated into 10 ml of sterile TSBYE and incubated at 37° C. for 18-22 h.

To select for spore formers, all cultures were subjected to heat treatment at 100° C. for 30 min to eliminate the vegetative cells. The cultures were then streaked onto TSAYE and incubated at 37° C. for 18-22 h.

Representative colonies from TSAYE agar plates were Gram stained and microscopically examined to determine the morphologies of the microorganisms isolated from the intestinal tracts of chicken. In addition, representative colonies from TSAYE agar plates were stained using 5% Malachite Green solution and examined microscopically for spore-formers.

Biochemical tests were performed to putatively identify all bacteria isolated from the intestinal tracts. A biochemical test kit, API 50 CH (bio Merieux) was used to identify various bacteria based on the fermentation profiles of 49 carbohydrates. After establishing the fermentation profiles of all bacteria isolated from the chicken intestinal tract, the API 50 CHB/L was used to identify Bacillus subtilis PB6 from the rest of the bacteria. The carbohydrate fermentation profiles were computed using the APILAB Plus software against a database, where the percentage of identification that is equal or greater than 99.9 is considered as excellent match. No identification will be provided if the percent identification is less than 80.

Antagonistic Assays

Putative strains of *Bacillus subtilis* PB6 were grown in TSBYE broth and incubated at 37° C. *Clostridium perfringens* ATCC 13124 was used as the indicator-organism to screen against microorganisms isolated from the intestinal tract of chicken. Isolated colonies of *C. perfringens* were inoculated into thioglycollate broth at 37° C. under anaerobic condition using Anaerogen Pak (Oxoid). An overnight culture of *C. perfringens* was streaked (perpendicular) onto the surface of TSAYE agar using a sterile cotton swap. An overnight culture containing the putative strain of *Bacillus subtilis* PB6 was then streaked across the same agar plates bisecting the streak-line of *C. perfringens*. All inoculated plates were incubated at 37° C. under 5% $CO_2$. After 24 h of incubation, antagonistic effects of the test-organisms against the indicator-bacteria can be observed by the appearance of clear zones surrounding the junctions of the streak-lines indicating the inhibitory effect of one organism against the other.

Thermal Treatment of Cells, Spores and Fermented Extracts of *Bacillus subtilis* PB6

Putative cells or spores of *Bacillus subtilis* PB6 were grown overnight for 18 h at 37° C. in a shaker incubator set at 100 rpm. A 1-ml volume of overnight culture was added to 9 ml of buffered peptone water (BPW) in a test tube and subjected to heat treatment at 90 and 100° C. for 2, 5 and 10 min, respectively. Similarly, fermented extracts or filtrates of *Bacillus subtilis* PB6 were heated at 70, 80, 90, 100, and 121° C. for 15 min. To ensure complete and uniform heating, the water level in the water bath was maintained above the level of the heating menstruum. After heating, the respective tubes for the different heating times at 90 or 100° C. were immediately placed in an ice water bath to prevent further destruction of the cells.

Effect of pH 2 on Spores of *Bacillus subtilis* PB6

An acidic solution of pH 2 was prepared by adding 0.2 ml 10 M HCL into 200 ml deionized water. A spore suspension was prepared by diluting 1000× in sterile deionized water (pH 6) and pre-heated at 80° C. for 20 min. The spore suspension was then inoculated into the acidic solution (pH 2) and incubated at 40° C. for 90 min. Viable cell counts were determined at 0, 30, 60 and 90-min intervals.

Effect of pH 6 and 0.75% Bile on Spores of *Bacillus subtilis* PB6

A concentration of 0.75% bile was added into an acidic solution (pH 2) and adjusted to a final pH of 6.0 using NaOH (12 M). To simulate pelleting conditions and the pH conditions of gizzard and small intestine, a pre-heat treated (80° C., 20 min) spore suspension was added into a HCL solution (pH 2) and incubated at 40° C. for 90 min. After 90 min of incubation, contents from the pH 2 solution were transferred to another flask containing 0.75% bile solution (pH 6) and then incubated at 40° C. for another 90 min. Finally, aliquots from the 0.75% bile solution (pH 6) were removed and diluted in BPW at 0, 30, 60 and 90 min and spread-plated onto TSAYE for viable cells.

Viable Cell Counts

Both vegetative cells and spores of *Bacillus subtilis* PB6 were diluted in buffered peptone water (BPW) and plated onto Tryptic Soy Agar supplemented with 6 g per liter of yeast extract (TSAYE) to confirm the numbers of viable cells. Spore suspension was heat-treated at 80° C. for 20 min, aseptically diluted into buffered peptone water (BPW) before spread-plated onto TSAYE for viable cell counts. Similarly, unheated spore suspension was also diluted and spread-plated onto TSAYE for viable cell counts. All media plates were incubated at 30° C. for 18 h. In terms of thermal inactivation studies, viable cell counts were plotted with respect to heating times and D-values (min) were derived from the gradient[31][1] of these graphs. D-value is defined as the time taken in minutes for a bacterial population to decrease by 1-log at a specific temperature (° C.).

Well Diffusion Assay

A modified agar-well diffusion method (Tagg and McGiven 1971) was used to examine the anticlostridial activity of filtrates from the fermented extracts or filtrates of *Bacillus subtilis* PB6. An overnight culture of *C. perfringens* ATCC 13124 or *C. difficile* was used as an indicator strain for the routine anticlostridial activity assays. Thioglycollate agar was tempered to 45° C. before being inoculated with overnight culture of the indicator strain. A 20-ml volume of this mixture was then poured onto each sterile petri-plate and allowed to solidify at room temperature for 1 h. The wells (0.75 cm diameter×1.0 cm depth) in the plate count agar were aseptically created by a hole-borer. A volume of 100 µl sample containing fermented extracts or filtrates of *Bacillus subtilis* PB6 was then placed in each well. In a similar manner, overnight cultures of *Streptococcus pneumoniae, Campylobacter jejuni, Campylobacter coli,* and *Helicobacter pylori* were mixed into suitable agar media and used as indicator organisms to test the effect of cells or fermented broth of *Bacillus subtilis* PB6. All culture plates were incubated at 37° C. for 18 h.

Characterization of Antimicrobial Compound

For production of the antimicrobial compound, *Bacillus subtilis* PB6 was grown aerobically in TSBYE for 18 h at 37° C. with shaking at 100 rpm. Bacteria cells were removed from the culture using a 0.22-µm (Sartorius) filter disc. Some of the filtrate was collected and stored overnight at 4° C. to observe the effect of refrigeration temperature on the filtrate. The filtrates collected were subjected to treatments with pronase, pepsin (final concentration of 1 mg per ml) for 1 h at 37° C. and trypsin (final concentration of 1 mg per ml) for 12 h at 37° C., and catalase (final concentration of 0.5 mg per ml).

Animal Trial Design

Four hundred one-day old healthy broilers (Wuxi Broiler Breeding Group Co. Ltd.) were randomly divided into two treatments including the controls. Each treatment comprised five replicates with 40 birds of mixed sex per replicate during the starter period (0-21 days). On day 21, twelve male and twelve female birds were selected randomly from each replicate and separated for the remaining trial period, resulting in 10 replicates (12 birds per replicate) per treatment for the finisher period (22-42 days).

Bird Management

The diets were formulated with a crude protein content of 20 and 18% for the starter and finisher diets, respectively. In the treatment 3 kg/T feed of PB6 filtrate containing the antimicrobial compound was included in the diet. The calculated metabolisable energy for both diets was approximately 2860 kcal/kg. Natural light was available during the day and dim lighting was provided during the nights to ensure continuous feeding. Water was supplied *ad libitum*.

Statistical Analysis

Analysis of variance and statistical difference between treatments were determined using SPSS and Duncan's Multiple Range.

RESULTS

Identification of Putative *Bacillus subtilis* PB6

PB6 was identified with 92% ID as being a *Bacillus* spp. (*Bacillus megaterium*) using the API biochemical test (Table 1). The fermentation profile of PB6 was compared to a API's LAB database, where the identity of the strain was expressed as the percentage of identification (% ID) that is based on the calculation of how closely the profile corresponds to the taxon relative to all the other taxa in the database (Table 1). PB6 was further confirmed as *Bacillus subtilis* using the ribotyping technique (FIG. 2). Cells of PB6 have been deposited with the American Type Culture Collection, Manassas, Va. on May 8, 2005. and have been assigned accession number PTA-6737, and all restrictions imposed by the depositor on the availability to the public of the deposited material will be irrevocably removed upon the granting of the patent.

TABLE 1

The API sugar profiles of *Bacillus subtilis* PB6

| Sugar profile | PB6 | *Bacillus subtilis* | *Bacillus megaterium* |
|---|---|---|---|
| Glycerol | + | + | +/− |
| Erythritol | − | − | − |
| D-Arabinose | − | − | − |
| L-Arabinose | + | + | +/− |
| Ribose | + | + | +/− |
| D-Xylose | + | +/− | +/− |
| L-Xylose | − | − | − |
| Adonitol | − | − | − |
| β Methyl-D-Xyloside | + | − | − |
| Galactose | + | − | +/− |
| Glucose | + | + | + |
| Fructose | + | + | + |
| Mannose | − | + | − |
| Sorbose | − | − | − |
| Rhamnose | − | − | − |
| Dulcitol | − | − | − |
| Inositol | + | +/− | +/− |
| Mannitol | + | + | +/− |
| Sorbitol | + | + | +/− |
| α Methyl-D-Mannoside | − | − | − |
| α Methyl-D-Glucoside | + | + | +/− |
| N-Acetyl-Glucosamine | − | +/− | + |
| Amygdalin | + | +/− | +/− |
| Arbutin | − | + | +/− |
| Esculin | + | + | +/− |
| Salicin | + | + | +/− |
| Cellobiose | + | + | +/− |
| Maltose | + | + | + |
| Lactose | + | − | +/− |
| Melibiose | + | +/− | +/− |
| Sucrose | + | + | + |
| Trehalose | + | + | + |
| Inulin | − | + | +/− |
| Melezitose | − | − | +/− |
| Raffinose | + | +/− | +/− |
| Starch | + | + | +/− |
| Glycogen | + | + | +/− |
| Xylitol | − | − | − |
| Gentiobiose | + | + | +/− |
| D-Turanose | + | +/− | +/− |
| D-Lyxose | − | − | − |
| D-Tagatose | − | − | − |
| D-Fucose | − | − | − |
| L-Fucose | − | − | − |
| D-Arabitol | − | − | − |
| L-Arabitol | − | − | − |
| Gluconate | − | − | − |
| 2-Keto-gluconate | − | − | − |
| 5-Keto-gluconate | − | − | − |
| ONPG | − | + | +/− |

TABLE 1-continued

The API sugar profiles of *Bacillus subtilis* PB6

| Sugar profile | PB6 | *Bacillus subtilis* | *Bacillus megaterium* |
|---|---|---|---|
| Arginine | − | − | − |
| Lysine | − | − | − |
| Omithine | − | − | − |
| Sodium Citrate | − | − | − |
| Sodium thiosulfate | − | − | − |
| Urea | − | − | − |
| Tryptophane | − | − | − |
| Indole | − | − | − |
| Sodium pyruvate | + | + | +/− |
| Kohn's gelatin | + | + | + |
| $NO_2$ production | − | +/− | +/− |

*Bacillus subtilis* PB6 was then confirmed using the ribotyping technique (FIG. 2).

Antagonistic Screening Against *Clostridium perfringens*

Cells and fermented extracts of *Bacillus subtilis* PB6 exhibit antimicrobial activities against *C. perfringens*, *C. difficile*, *Campylobacter jejuni*, *Campylobacter coli*, and *Streptococcus pneumoniae* (Table 2).

Table 3 presents data from a Well Diffusion Assay, wherein cultures of *Bacillus subtilis* PB6 were grown in the recited temperatures for 24 h before filtrates were collected and placed into the wells of the agar seeded with *Clostridium perfringens* ATCC 13124 as the indicator-organism.

TABLE 2

Effect of Fermented Extracts of *Bacillus subtilis* PB6 on Human Pathogens

| Organisms | Area of zone ($mm^2$) | Inhibition Relative to Control (%) |
|---|---|---|
| *Clostridium perfringens** | 336 | 100 |
| *Streptococcus pneumoniae* | 210 | 63 |
| *Campylobacter jejuni* | 528 | 157 |
| *Campylobacter coli* | 487 | 145 |
| *Clostridium difficile* | 917 | 273 |

*Control indicator-microorganism

TABLE 3

Effect of Culture Growth Temperature on the Anti-Clostridial Factors

| Growth Temperature (° C.) | Zone of Inhibition ($mm^2$) | Percent Relative Inhibition (%) |
|---|---|---|
| 37* | 302 | 100 |
| 41 | 27 | 9 |
| 45 | 0 | 0 |
| 50 | 0 | 0 |

*denotes control

Thermal Treatment of Cells, Spores and Fermented Extracts of *Bacillus subtilis* PB6

When vegetative cells of *Bacillus subtilis* PB6 were heat-treated at 90° C. for 2-10 min, approximately 5 to 6 log reductions in viable cell counts were observed (data not shown). Compared to the other *Bacillus* strains tested, vegetative cells of *Bacillus subtilis* PB6 demonstrated the highest heat resistance with a D-value of 0.44 min (Table 4). The D-values at 100° C. for vegetative cells of *Bacillus* subtilis PB6 was 0.41 min (Table 4). The D-values at 90 and 100° C. for spores of Bacillus subtilis PB6 was 24 and 1.07 min, respectively (Table 4).

TABLE 4

Thermal death time [a] (D-values) of Bacillus subtilis PB6

| Bacteria | D-values [a] (min) | |
|---|---|---|
| | 90° C. | 100° C. |
| B. subtilis PB6 [b] | 0.44 | 0.41 |
| B. subtilis PB6 [c] | 24 | 1.07 |

[a] Defined as time taken in minutes for a bacterial population to decrease by 1-log at a specific temperature (° C.);
[b] vegetative cells isolated from chicken GI tract;
[c] spores isolated from chicken GI tract.

Stability of the Antimicrobial Compound of Bacillus subtilis PB6

The anticlostridial factor(s) within the fermented extracts of Bacillus subtilis PB6 remain active after heat treatment at 70, 80, 90, 100, and 121° C. for 15 min and overnight storage at 4° C. (Table 5).

TABLE 5

Effect of Heat Treatment on the Anti-Clostridial Factor(s) produced by Bacillus subtilis PB6

| Heat treatment | Zone of Inhibition (mm²) | Percent Relative Inhibition (%) |
|---|---|---|
| Unheated* | 336 | 100 |
| 70° C. | 336 | 100 |
| 80° C. | 302 | 90 |
| 90° C. | 302 | 90 |
| 100° C. | 302 | 90 |
| 121° C. | 302 | 90 |

*denotes control

The anticlostridial factor(s) within the fermented extracts of Bacillus subtilis PB6 remain active after treatment with trypsin (Table 6). Wells containing untreated filtrate, stored either at 4 or 25° C. with the latter serving as control.

TABLE 6

Effect of Treatment with Trypsin on the Anti-Clostridial Factors

| Treatment | Area of zone (mm²) | Inhibition Relative to Control (%) |
|---|---|---|
| Untreated - 25° C.* | 446 | 100 |
| Untreated - 4° C. | 408 | 90 |
| Trypsin | 270 | 60 |

*denotes control

The antimicrobial compound was stable to treatment with catalase and a range of proteases such as pronase, and pepsin (Table 7). Wells containing TSBYE (pH 7.0), TSBYE at pH 6.3, with untreated filtrate and hydrogen peroxide serving as controls.

TABLE 7

Effect of Treatment with Catalase, Pronase, and Pepsin on the Anti-Clostridial Factors

| Treatment | Area of zone (mm²) | Inhibition Relative to Control (%) |
|---|---|---|
| Untreated* | 302 | 100 |
| Pronase | 132 | 44 |

TABLE 7-continued

Effect of Treatment with Catalase, Pronase, and Pepsin on the Anti-Clostridial Factors

| Treatment | Area of zone (mm²) | Inhibition Relative to Control (%) |
|---|---|---|
| Pepsin | 239 | 79 |
| Catalase | 270 | 89 |
| Hydrogen peroxide | 1150 | 381 |
| TSBYE (pH 7.0) | 0 | 0 |
| TSBYE (pH 6.3) | 0 | 0 |

*denotes control

Effect of pH and Bile Salts on Spores of Bacillus subtilis PB6

When preheated spores of Bacillus subtilis PB6 (80° C., 20 min) were incorporated into acidified solution (pH 2) and incubated at 40° C. for 90 min, negligible or no major decrease in viable cells was observed (Table 8).

TABLE 8

Effect of pH 2 on germination of spores[a] of Bacillus subtilis PB6

| | Control[b] | | pH 2 (HCl) solution | |
|---|---|---|---|---|
| Time (min) | CFU per ml | % spore germination | CFU per ml | % spore germination |
| 0 | $9.2 \times 10^9$ | 100 | $8.5 \times 10^9$ | 100 |
| 30 | $7.4 \times 10^9$ | 80 | $7.4 \times 10^9$ | 87 |
| 60 | $7.3 \times 10^9$ | 79 | $7.7 \times 10^9$ | 91 |
| 90 | $6.6 \times 10^9$ | 72 | $8.3 \times 10^9$ | 98 |

[a] Bacillus spores were initially heat-treated at 80° C. for 20 min before incorporating into sterile deionized water (pH 5.7–5.8) and pH 2 solution;
[b] control indicates B. subtilis PB6 spores were preheated at 80° C. for 20 min before incorporating into sterile deionised water (pH 5.7–5.8).

After 90 min of incubation in acidified solution (pH 2), the percentage of Bacillus spore germination was still at 98% (Table 8). Spores of Bacillus subtilis PB6 were found to survive and germinate (28%) when treated at pH 2 and then added to pH 6 solution containing 0.75% bile and incubated for 90 min (Table 9).

TABLE 9

Effect of pH and 0.75% bile on germination of spores[a] of Bacillus subtilis PB6

| | Control[b] | | pH[c] and 0.75% bile treatment | |
|---|---|---|---|---|
| Time (min) | CFU per ml | % spore germination | CFU per ml | % spore germination |
| 0 | $6.3 \times 10^8$ | 100 | $5.6 \times 10^9$ | 100 |
| 30 | $5.7 \times 10^8$ | 90 | $1.3 \times 10^9$ | 23 |
| 60 | $3.6 \times 10^8$ | 57 | $1.8 \times 10^9$ | 32 |
| 90 | $2.9 \times 10^8$ | 41 | $1.6 \times 10^9$ | 28 |

[a] All Bacillus spores were initially preheat-treated at 80° C. for 20 min;
[b] Bacillus spores were incubated at 40° C. and pH 6 (0.75% bile) alone;
[c] Bacillus spores were incubated at 40° C. and pH 2 for 90 min before incorporating into pH 6 solution containing 0.75% bile.

Effect of PB6 filtrate on the FCR of Broilers

The effect of adding 3 kg/T PB6 filtrate containing the antimicrobial compound on the feed conversion ration (FCR) of broilers was studied. The results (Table 10) show that the compound improved the FCR of birds in both the starter and finisher periods compared to the control in which no PB6 antimicrobial compound was added.

TABLE 10

Effect of the antimicrobial compound from PB6 on performance of broilers.

| | Weight gain of starter (g) | Feed efficiency of starter (0–21 d) | Weight gain of finisher (g) | Feed efficiency of finisher | Weight gain of total period (g) | Feed efficiency of total period (22–42 d) |
|---|---|---|---|---|---|---|
| Control | 604 ± 6$^a$ | 1.52 ± 0.12$^a$ | 864 ± 126$^a$ | 2.63 ± 0.28$^a$ | 1474 ± 150$^a$ | 2.16 ± 0.16$^a$ |
| Treatment (3 kg/T) | 621 ± 4$^b$ | 1.47 ± 0.14$^b$ | 969 ± 72$^a$ | 2.39 ± 0.28$^a$ | 1591 ± 59$^a$ | 2.02 ± 0.13$^a$ |

The foregoing description comprises illustrative embodiments of the present inventions. The foregoing embodiments and the methods described herein may vary based on the ability, experience, and preference of those skilled in the art. Merely listing the steps of the method in a certain order does not necessarily constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

What is claimed is:

1. A composition, comprising:
a biologically pure culture of viable bacterial cells of the *Bacillus subtilis* strain deposited under ATCC Accession No. PTA-6737 and a pharmaceutically acceptable carrier.

2. The composition according to claim 1, wherein the viable bacterial cells are stable for 90 minutes upon exposure to pH 6 and to 0.75% bile salt at pH 2.

3. The composition according to claim 1, further comprising fermented extracts produced by the cells, the fermented extracts having antimicrobial activities against human and non-human animal pathogens.

4. The composition according to claim 3, wherein the human and non-human animal pathogens are selected from the group consisting of *Clostridium, Campylobacter, Streptococcus* and *Helicobacter*.

5. The composition according to claim 3, wherein the fermented extracts retain 90% antimicrobial activity against *Clostridium perfringens* upon exposure to 121° C. for 15 minutes.

6. The composition according to claim 3, wherein the fermented extracts retain antimicrobial activity against *Clostridium perfringens* of 60% upon treatment with trypsin, of 44% upon exposure to pronase, and of 79% upon exposure to pepsin.

* * * * *